United States Patent [19]

Davis

[11] Patent Number: 4,662,919
[45] Date of Patent: May 5, 1987

[54] NITROGEN REJECTION FRACTIONATION SYSTEM FOR VARIABLE NITROGEN CONTENT NATURAL GAS

[75] Inventor: Ruth A. Davis, Allentown, Pa.

[73] Assignee: Air Products and Chemicals, Inc., Allentown, Pa.

[21] Appl. No.: 831,374

[22] Filed: Feb. 20, 1986

[51] Int. Cl.⁴ ............................................. F25J 3/02
[52] U.S. Cl. .......................................... 62/25; 62/29; 62/34; 62/40
[58] Field of Search ................. 62/25, 29, 33, 34, 40

[56] References Cited

U.S. PATENT DOCUMENTS

| 3,797,261 | 3/1974 | Juncker et al. | 62/40 |
| 4,411,677 | 10/1983 | Pervier et al. | 62/25 |
| 4,453,956 | 6/1984 | Fabbri et al. | 62/33 |
| 4,501,600 | 2/1985 | Pahade | 62/34 |
| 4,504,295 | 3/1985 | Davis et al. | 62/30 |

Primary Examiner—Ronald C. Capossela
Attorney, Agent, or Firm—Willard Jones, II; James C. Simmons; E. Eugene Innis

[57] ABSTRACT

The present invention is directed to a gas separation system for separating or rejecting nitrogen from a natural gas feed containing nitrogen, over a wide range of nitrogen concentrations, under elevated pressure using a single distillation column with two intermediate side condensers and a closed loop heat pump which reboils and partially refluxes the column. The lower of the intermediate condensers is cooled by heat exchange with the heat pump fluid and the overhead nitrogen fraction of the column. The upper of the intermediate condensers is cooled by heat exchange with the overhead nitrogen fraction of the column. The process can handle feeds with increasing nitrogen composition and more than 100 vppm carbon dioxide. The process provides a high methane recovery over the entire feed range, and provides a nitrogen product having an elevated pressure suitable for recycling and reinjection into an oil or gas well to maintain well head pressure.

13 Claims, 2 Drawing Figures

NITROGEN REJECTION FRACTIONATION SYSTEM FOR VARIABLE NITROGEN CONTENT NATURAL GAS

TECHNICAL FIELD

The present invention is directed to the separation of nitrogen from natural gas containing nitrogen over a wide concentration range to form nitrogen and natural gas product streams under elevated pressure without incorporating a means for recompression of the separated products.

BACKGROUND OF THE PRIOR ART

Petroleum production methods currently are utilizing high pressure nitrogen injection to maintain well head pressure for enhanced oil and gas recovery. As nitrogen is injected, the natural gas from the well containing methane and associated hydrocarbon liquids also contains nitrogen which increases in amount over the life of the nitrogen injection project. For this reason, natural gas containing nitrogen must be separated to reject the nitrogen and form purified natural gas feedstocks suitable for utilization as fuel or chemical feedstocks.

U.S. Pat. No. 3,797,261 discloses the separation of natural gas containing nitrogen into a low-nitrogen fraction and a high nitrogen fraction by distillation in a single distillation column by expanding the high-nitrogen fraction with the performance of work and using the resulting refrigeration to condense vapor in the upper section of the column while additional reflux is provided by vaporizing a recycle medium in heat exchange relation with vapor in the column. The high-nitrogen mixture, having been expanded, is exhausted at atmospheric pressure.

U.S. Pat. No. 4,411,677 discloses a process for rejecting nitrogen from a natural gas feed containing nitrogen over a broad range of compositions, under elevated pressure using a single distillation column, and a closed loop methane heat pump which reboils and refluxes the column. An intermediate reflux condenser is cooled by both the heat pump and overhead nitrogen stream of the column. A mixed cryogenic refrigerant can be used in the heat pump as an alternative to the methane heat pump medium. The process provides a high methane recovery over the entire feed range and a pressurized nitrogen product stream that can be used for recycling and reinjection into an oil or gas well to improve head pressure.

U.S. Pat. No. 4,504,295 discloses a process for the recovery of methane, nitrogen and natural gas liquids from a natural gas feed stream wherein the recovery can be made at high pressure by integration of a nitrogen rejection stage including a heat pump driven distillation column and a natural gas liquid stage. Nitrogen can be rejected over a wide range of nitrogen concentration of the feed stream.

SUMMARY OF THE INVENTION

The process of the present invention provides a system for separating nitrogen from a pressurized feed containing natural gas and nitrogen over a broad range of nitrogen concentrations in a single distillation column to form a pressurized nitrogen product stream and a pressurized natural gas product stream. The process of the invention condenses an overhead vapor of an upper section of the column by heat exchange with a first closed loop refrigerant to provide reflux to the column, condenses intermediate vapor at two locations along the intermediate section of the column above the feed entry point of the column. In the upper of the two condensers the vapor is condensed by heat exchange with the nitrogen product stream from the overhead of the column, and in the lower of the two condensers the vapor is condensed by heat exchange with both the nitrogen product stream and a second closed loop refrigerant. Preferably, the first and second closed loop refrigerants comprise the first and second portions of a circulating refrigeration fluid in a closed heat pump such that the refrigeration fluid is compressed, cooled in heat exchange with the bottom liquid of the distillation column thereby providing reboiler heat to the column, subcooled to a temperature sufficient to form and provide the second closed loop refrigerant, and further subcooled to a temperature sufficient to form the first closed loop refrigerant.

The process of the present invention is capable of separating or rejecting nitrogen from natural gas containing nitrogen over a wide range of nitrogen content. Generally, the range of nitrogen content is from about 5 to about 85 volume percent.

The process of this invention incorporates a heat pump fluid of methane, however a mixed cryogenic refrigerant can be used to adapt the cycle efficiently to different feeds and product specifications.

DETAILED DESCRIPTION OF THE PREFERRED EMBODIMENT

Figure 1:
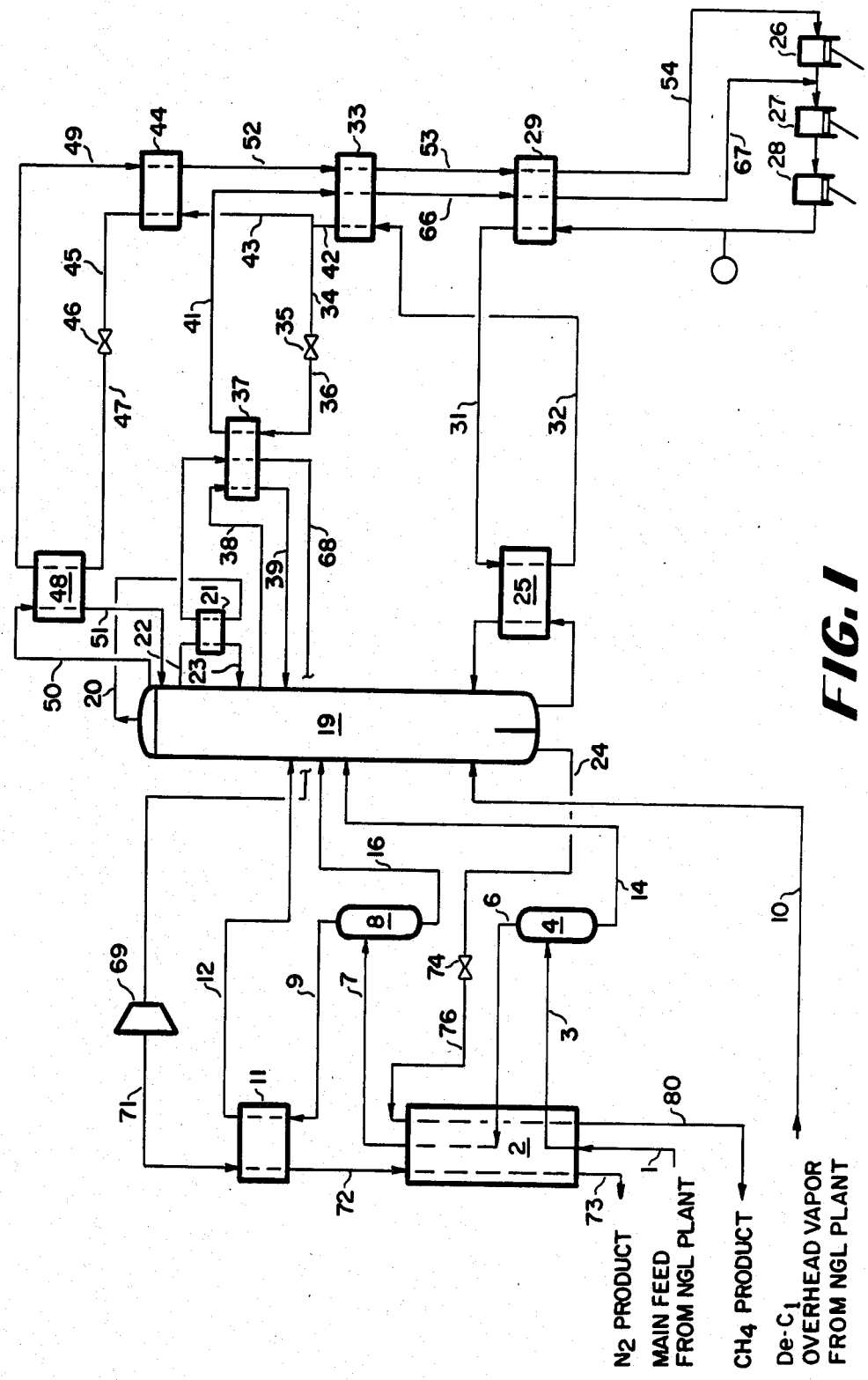
FIG. 1 is a schematic flow diagram of a preferred embodiment of the invention for a process for separating nitrogen from natural gas containing nitrogen.

Enhanced oil recovery projects employing high pressure nitrogen result in produced natural gas with increasing amounts of contained nitrogen. Nitrogen must be rejected from the lean natural gas to upgrade the gas heating value and make it acceptable for pipeline sales. The process of this invention provides a system for separating or rejecting the nitrogen from the variable composition natural gas and providing the nitrogen product stream at an elevated pressure thereby decreasing the need for recompression prior to recycle for enhanced recovery.

Referring to the drawing, a natural gas feed stream from an oil reservoir or gas field maintained at pressure by high pressure nitrogen injection enters a natural gas liquids recovery plant, not shown, where ethane and heavier hydrocarbons are separated as liquids. The natural gas containing nitrogen, at a pressure of about 400 psia, is fed to the process of the present invention as shown in the drawing. There are two streams which come from the natural gas liquids recovery plant, the first, line 1, is the primary feed gas, nitrogen containing natural gas, and the second, line 10, is the secondary gas feed, demethanized natural gas recovery plant overhead vapor. The primary feed gas enters the present process in line 1 and is cooled in the main feed heat exchanger 2. The cooled primary feed gas is passed in line 3 to separator 4 where liquid is removed. Vapor from separator 4 is passed in line 6 for further cooling in the main exchanger 2 and is fed in line 7 to separator 8. Vapor from separator 8 is sent through line 9 to cold feed heat exchanger 11. The cooled vapor from heat exchanger 11 is passed via line 12 and together with liquid cuts from the separators 4 and 8 via lines 14 and 16 are introduced to distillation column 19 at increasingly higher, and accordingly colder, trays of the distillation column. The secondary feed gas stream enters the process in line 10 and is fed to the bottom portion of the distillation column 19.

A fractionation is performed in distillation column 19, overhead vapor product comprising a vapor rich in nitrogen is removed via line 20, and a bottoms liquid stream comprising liquefied natural gas and heavier hydrocarbons is removed via line 24. The reboiler duty for column 19 is provided in reboiler 25 by the heat pump fluid in line 31.

An external heat pump cycle heat pump system is employed having compressors 26, 27, and 28 for the staged compression of nearly pure methane, which is used as the circulating heat pump fluid. Compressed heat pump fluid exiting compressor 28 is passed to gas heat exchanger 29 and is therein cooled. The cold compressed heat pump fluid is passed via line 31 to reboiler 25 to provide reboiler heat wherein the heat pump fluid is totally condensed. The liquid heat pump fluid exiting the reboiler in stream 32 is subcooled in warm subcooler 33. Subcooled liquid heat exchange fluid via line 42 is split into two streams in lines 34 and 43. The subcooled heat pump fluid in line 34 is flashed at 35 to an intermediate pressure and is passed in line 36 to be vaporized in the lower side condenser 37 to provide intermediate reflux in column 19 by cooling an intermediate fraction withdrawn from column 19 in line 38 and partially condensed in side condenser 37 to form a reflux stream in line 39 which is introduced back into column 19. The intermediate reflux provided by side condenser 37 alternatively can be provided by heat exchange directly within column 19 in lieu of side condenser 37 as depicted external to column 19 in the drawing. The lower intermediate reflux is provided at a point between the upper intermediate condenser and the highest feed to column 19. After being vaporized in the side condenser 37, the heat pump fluid at an intermediate pressure exits in line 41. Subcooled heat pump fluid in line 43 is further subcooled in cold subcooler 44 and is passed in line 45 to the coldest part of the plant where it is flashed at 46 and fed in line 47 to the overhead condenser 48 where the heat pump fluid is revaporized and exits the condenser in line 49. The overhead condenser 48 provides condensing duty for the overhead vapor from the distillation column in line 50 which becomes reflux to the column in line 51. Low pressure vapor in line 49 is returned through cold subcooler 44 and further in line 52 to warm subcooler 33 and is further passed in line 53 to gas-gas exchanger 29 prior to being returned in line 54 to the beginning of recompression stage in compressor 26. The heat pump fluid from side condenser 37 in line 41 is rewarmed in warm subcooler 33 is passed in line 66 to the gas-gas exchanger 29 prior to return in line 67 to compression stage at an intermediate position, between compressor 26 and compressor 27.

High pressure nitrogen from the overhead of the fractionation column in line 20 is used to cool an upper side condenser 21 to provide intermediate reflux in the column by cooling an intermediate fraction withdrawn from the column in line 22 and cooled in side condenser 21 to form a liquid stream in line 23 which is introduced back into column 19 as reflux. The intermediate reflux provided by side condenser 21 alternatively can be provided by heat exchange directly within column 19 in lieu of side condenser 21 as depicted external to the column in the drawing. The upper intermediate reflux in line 23 is provided at a point between the overhead condenser and the lower intermediate condenser. The nitrogen product stream from side condenser 21 is sent through side condenser 37. The high pressure nitrogen product in line 68 can be expanded to about 250 psia in expander 69 to provide extra refrigeration as desired from the nitrogen which is sent in line 71 through cold exchanger 11 and further through line 72 to the main feed heat exchanger 2 where final refrigeration recovery from the cold nitrogen occurs. Product nitrogen at an elevated pressure exits the main feed heat exchanger 2 in line 73 and may be recycled or vented.

Hydrocarbon products from the bottom of the column in line 24 are flashed at 74 and sent to main feed heat exchanger 2 to provide condensing duty for the feed. Product natural gas is removed in line 80.

Figure 2:
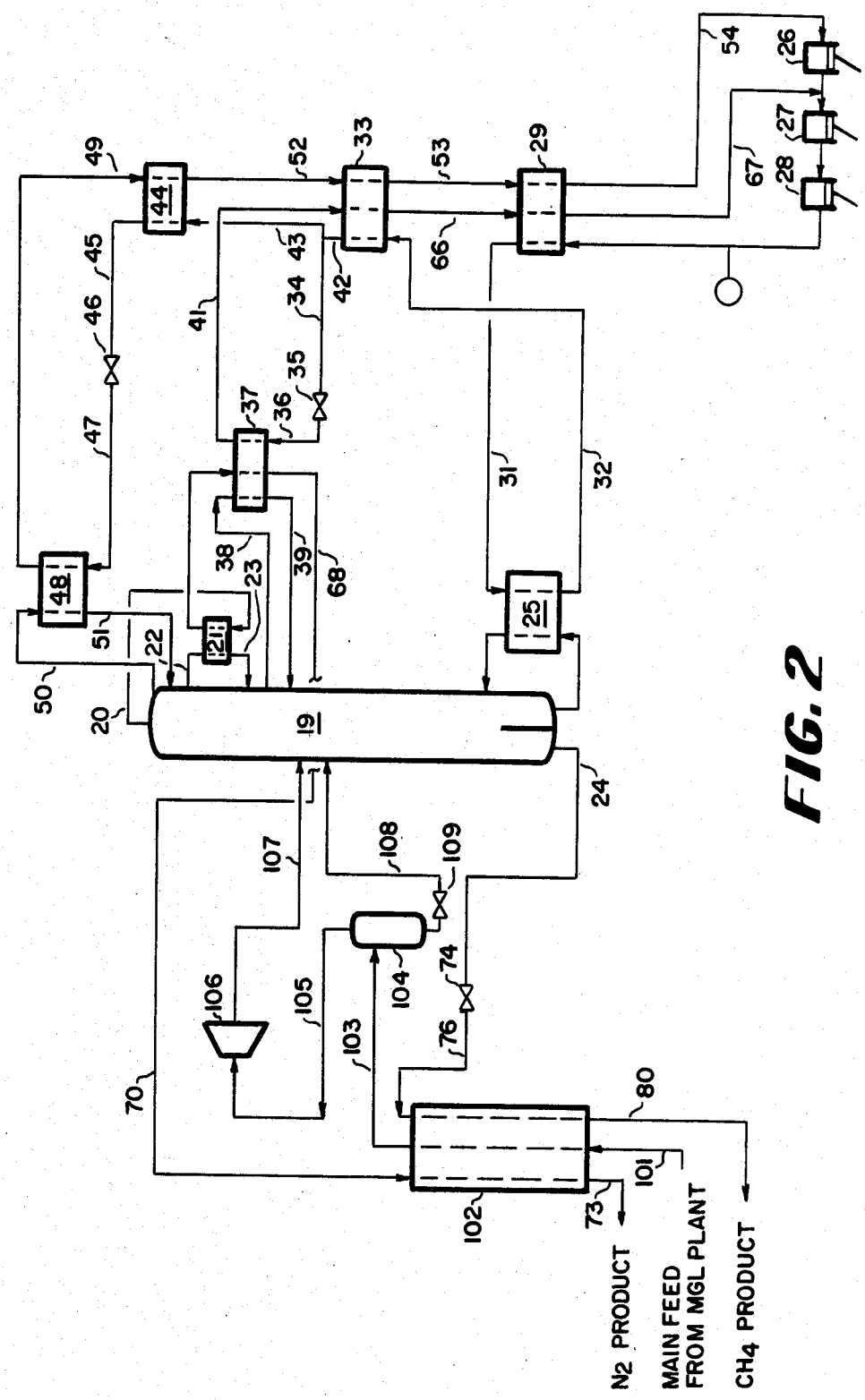
FIG. 2 is a schematic flow diagram of an alternate embodiment of the invention for a process for separating nitrogen from natural gas containing nitrogen.

Optionally, as shown in FIG. 2, the process front end can operate with only one feed and one feed separator. In such a case, the feed gas in stream 101 would continue through heat exchanger 102. The cooled feed is fed, via line 103, to separator 104. The overhead of separator 104, line 105, is expanded through expander 106 and fed, via line 107, to distillation column 19. The liquid from separator 104 is expanded through a J-T valve 109 and introduced, via line 108, into distillation column 19. The high pressure nitrogen product in line 68 is warmed in heat exchanger 102 and exits the process as stream 73. The remaining stream configurations are identical to the embodiment of FIG. 1 and are numbered the same.

The multiple side condenser arrangement of the present invention achieves column reflux adjustment by effectively utilizing the cold nitrogen overhead vapors for refrigeration recovery. When the nitrogen content in the natural gas feed is small, the cold overhead vapor can provide only a small percentage of the total nitrogen column reflux requirements. The majority of the intermediate reflux is delivered by the lower side condenser. As the nitrogen content in the feed gas continues to rise, the upper side condenser generates an increasing amount of the column intermediate reflux and column operation efficiency is maintained.

The upper side condenser changes the temperature profile in the column refluxing section, warming the lower side condenser reflux. This phenomenon increases the allowable pressure of the interstage heat pump refrigerant boiling in the exchanger. The utility of interstage heat pump refrigerant is also maintained at higher feed nitrogen compositions because of the tendency for continuously colder column reflux is partially offset.

The multiple condenser arrangement can efficiently and continuously follow the nitrogen-methane fractionation refrigeration demands which change with increasing nitrogen in the natural gas feed. Additionally, the effective integration of the side condensers with both nitrogen and heat pump refrigeration recovery increases the utility of intermediate pressure heat pump fluid for column reflux at higher nitrogen contents in the natural gas. Both effects lower the heat pump fluid compression power required to drive the high pressure single column separation when the plant operates in the mid range feed nitrogen compositions.

The principal advantage of the multiple side condenser arrangement for variable content nitrogen-methane fractionation is the heat pump savings that can be achieved from distillation efficiency and effective refrigeration integration.

The process, either with or without natural gas liquids recovery, employs multiple feeds to the column to reduce the amount of reflux and reboil in the column. FIG. 1 depicts a system with a number of separators which is part of the preferred embodiment, but nevertheless, the process of the present invention can be carried out with fewer feed separators, as shown in FIG. 2. The process of the present invention is suitable for natural gas streams with or without natural gas liquids recovery where the feed gas pressure is 350 psia or greater. The preferred range of operation of the distillation column is 300 to 400 psia. Fractionation above 400 psia will approach the critical pressure of nitrogen thus making operation impractical.

The product methane derived from the present process contains concentrations of nitrogen of about 1 to 3 volume percent and recovery of the hydrocarbons is about 99.5 percent.

Additionally, the high pressure distillation process has the added advantage of handling significant quantities of carbon dioxide, about 100 parts per million by volume (vppm) or higher, without solidification of the carbon dioxide.

The present invention provides a favorable energy consumption improvement over known nitrogen rejecting gas separation systems. As shown in the following example, the present invention rejects nitrogen at a reduced power requirement. The calculated power reduction is about three percent over other rejection systems.

EXAMPLE

Referring to FIG. 2. A feed gas stream containing 50 volume percent nitrogen and 50 volume percent natural gas hydrocarbons is introduced into the process, via line 101, at a pressure of 850 psia and a temperature of −73° C. The feed gas is cooled in the main feed exchanger 102 to a temperature of −100° C., prior to being sent to separator 104, via line 103. The bottoms of the separator, approximately 15 weight percent of line 103, is expanded and fed to distillation column 19 via line 108. The overhead of separator 104, line 105, approximately 85 weight percent of line 103, is expanded in expander 106 and is fed to distillation column 19 in line 107.

Two products are removed from the distillation column operating at 350 psia, a vapor rich in nitrogen is removed in line 20 and a liquid rich in natural gas hydrocarbons is removed in line 24. The overhead from the column accounts for approximately 60 weight percent of the feed to the column and has a composition of about 99.5 volume percent nitrogen and 0.5 volume percent natural gas. The bottoms from the column account for approximately 40 weight percent of the feed and has a composition of about 2 volume percent nitrogen and 98 volume percent natural gas hydrocarbons.

The present invention provides a favorable improvement over known nitrogen rejecting gas separation systems. As shown in Table I below, the present invention rejects nitrogen at a reduced power requirement over a commonly assigned patented cycle disclosed in U.S. Pat. No. 4,411,677. The calculated power reduction of over three percent is believed to be a significant reduction in gas separation systems, especially when this translates into smaller compressor equipment for heat pump compression.

TABLE I

|  | U.S. Pat. No. 4,411,677 | Present Invention |
| --- | --- | --- |
| Power Required, bhp/MMSCFD: | 59.50 | 57.50 |
| Improvement, percent: | — | 3.0 |

The basis of the evaluation was at 100 MMSCFD, at a natural gas product of 4173 lb-moles/hr, at 2 volume percent nitrogen in the product, a temperature of 30° C., and a product pressure of 250 psia.

The present invention has been described with reference to a preferred embodiment thereof. However, this embodiment should not be considered a limitation on the scope of the invention, which scope should be ascertained by the following claims.

I claim:

1. A process for separating nitrogen from a pressurized feed containing natural gas and nitrogen over a wide concentration range of 5 to 85 volume percent nitrogen in a single distillation column with two side intermediate condensers to form pressurized product streams of nitrogen and natural gas comprising:
    (a) cooling and separating the pressurized feed into separate multiple feeds to the column and distilling the cooled feeds in the distillation column to form a pressurized overhead vapor rich in nitrogen and a pressurized bottoms liquid rich in natural gas hydrocarbons;
    (b) condensing an overhead vapor of an upper section of the column by heat exchange with a first closed loop refrigerant to provide reflux to the column;
    (c) condensing in the upper of two side condensers an intermediate vapor from an intermediate section of the column between the overhead vapor condenser and the lower of the two side condensers by heat exchange with the overhead vapor without expansion to provide an intermediate reflux to the column, wherein the intermediate section vapor condensing with the overhead product stream increases with increasing nitrogen concentration in the feed; and
    (d) condensing in the lower of two side condensers an intermediate vapor from an intermediate section of the column between the upper of the two side condensers and the highest feed point by heat exchange with a second closed loop refrigerant and by heat exchange with the overhead vapor without expansion to provide reflux to the column, wherein the intermediate section vapor condensing with the overhead product stream increases with increasing nitrogen concentration in the feed.

2. The process according to claim 1 wherein the product stream nitrogen is reinjected into an oil or gas well to improve well head pressure.

3. A process according to claim 1 wherein the first and second closed loop refrigerants comprise first and second portions of a circulating refrigeration fluid in a closed loop heat pump wherein the refrigeration fluid is compressed; cooled; condensed in heat exchange with the bottoms in the column, thereby providing reboil heat to the column; subcooled to a temperature sufficient to form the second closed loop refrigerant; and further subcooled to a temperature sufficient to form the first closed refrigerant.

4. A process according to claim 3 wherein said circulating heat pump fluid comprises methane.

5. A process according to claim 3 wherein said circulating heat pump fluid comprises a mixed cryogenic refrigerant.

6. The process according to claim 1 wherein said feed cooling comprises cooling in a first portion of a main feed heat exchanger against the pressurized product streams to form a two-phase first feed stream; phase separating the condensed portion of the cooled first feed stream in a first separator to form a second feed liquid stream and a second feed vapor stream; cooling the second feed vapor stream in a cold feed heat exchanger to condense a portion thereof, separating the condensed portion of the second feed separator to form a third feed liquid stream and a third feed vapor stream; and introducing the second and third feed liquid streams and the third feed vapor stream to the single distillation column at increasingly colder sections, respectively.

7. A process according to claim 6 wherein the feed contains carbon dioxide in an amount greater than 100 parts per million by volume.

8. In a process for separating nitrogen from a pressurized feed containing natural gas and nitrogen consisting of cooling said pressurized feed and distilling the cooled feed in a single distillation column to form a pressurized overhead vapor rich in nitrogen and a pressurized bottoms liquid rich in natural gas hydrocarbons, the improvement for accommodating a wide concentration range of nitrogen in the feed and forming a pressurized product stream of nitrogen suitable for reinjection to maintain a well head pressure for enhanced oil or gas recovery comprising:
 (a) cooling and separating the pressurized feed into separate multiple feeds to the column;
 (b) condensing an overhead vapor of an upper section of the column by heat exchange with a first closed loop refrigerant to provide reflux to the column;
 (c) condensing in the upper of two side condensers an intermediate vapor from an intermediate section of the column between the overhead vapor condenser and the lower of the two side condensers by heat exchange with the overhead vapor without expansion to provide an intermediate reflux to the column, wherein the intermediate section vapor condensing with the overhead product stream increases with increasing nitrogen concentraton in the feed; and
 (d) condensing in the lower of two side condensers an intermediate vapor from an intermediate section of the column between the upper of the two side condensers and the highest feed point by heat exchange with a second closed loop refrigerant and by heat exchange with the overhead vapor without expansion to provide reflux to the column, wherein the intermediate section vapor condensing with the overhead product stream increases with increasing nitrogen concentration in the feed.

9. A process according to claim 8 wherein said first and second closed loop refrigerants comprise first and second portions of a circulating refrigeration fluid in a closed loop heat pump wherein the refrigeration fluid is compressed; cooled; condensed in heat exchange with the bottoms of said column, thereby providing reboil heat to the column; subcooled to a temperature sufficient to form the second closed loop refrigerant; and further subcooled to a temperature sufficient to form the first closed refrigerant.

10. The process according to claim 9 wherein said feed cooling comprises cooling in a first portion of a main feed heat exchanger against the pressurized product streams to form a two-phase first feed stream; phase separating the condensed portion of the cooled first feed stream in a first separator to form a second feed liquid stream and a second feed vapor stream; cooling the second feed vapor stream in a cold feed heat exchanger to condense a portion thereof, separating the condensed portion of the second feed separator to form a third feed liquid stream and a third feed vapor stream; and introducing the second and third feed liquid streams and the third feed vapor stream to the single distillation column at increasingly colder sections, respectively.

11. A process according to claim 10 wherein the feed contains carbon dioxide in an amount greater than 100 parts per million volume.

12. A process according to claim 9 wherein said circulating heat pump fluid comprises methane.

13. A process according to claim 9 wherein said circulating heat pump fluid comprises a mixed cryogenic refrigerant.

* * * * *